United States Patent [19]

Biziere et al.

[11] Patent Number: 4,613,603
[45] Date of Patent: Sep. 23, 1986

[54] COMPOUNDS WITH A NITROGEN-CONTAINING HETEROCYCLIC NUCLEUS, AND DRUGS IN WHICH THEY ARE PRESENT

[75] Inventors: Kathleen Biziere, Clapiers; Jean-Pierre Chambon, Montarnaud; André Hallot, Saint-Gely-du-Fesc, all of France

[73] Assignee: Sanofi, Paris, France

[21] Appl. No.: 752,740

[22] Filed: Jul. 8, 1985

[30] Foreign Application Priority Data

Jul. 11, 1984 [FR] France ................. 84 11039

[51] Int. Cl.[4] ............... C07D 401/04; A61K 31/53; A61K 31/505; A61K 31/445
[52] U.S. Cl. .................. 514/242; 514/275; 514/316; 514/318; 546/193; 546/187; 544/330; 544/331; 544/332; 544/182
[58] Field of Search ............ 544/182, 330, 331, 332; 546/193, 187; 514/242, 275, 316, 318

[56] References Cited

U.S. PATENT DOCUMENTS 4,467,087 8/1984 Durant et al. ................. 544/182

FOREIGN PATENT DOCUMENTS 0088593 9/1983 European Pat. Off. .
0090733 10/1983 European Pat. Off. .

*Primary Examiner*—John M. Ford
*Attorney, Agent, or Firm*—Stevens, Davis, Miller & Mosher

[57] ABSTRACT

The invention relates to compounds with a nitrogen-containing heterocyclic nucleus, of the general formula:

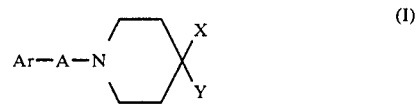

in which:
Ar represents a group

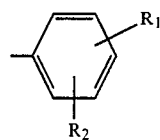

or a naphthyl group optionally substituted by a halogen, A represents a heterocyclic nucleus chosen from the group consisting of the pyridine, pyrimidine and triazine nuclei, and X and Y, taken separately, denote a hydrogen atom in one case and a group $OR_3$ (hydroxyl, carbamate or ester) in the other.

The invention also relates to a process for the preparation of these compounds and their application as drugs acting on the central nervous system.

11 Claims, No Drawings

COMPOUNDS WITH A NITROGEN-CONTAINING HETEROCYCLIC NUCLEUS, AND DRUGS IN WHICH THEY ARE PRESENT

The present invention relates to new heterocyclic compounds having valuable therapeutic properties on both the central and peripheral nervous systems.

In particular, the compounds according to the invention have anticonvulsant, hypnotic and analgesic actions on the central nervous system as well as actions on the circulatory system, in particular a platelet aggregation inhibiting action.

The compounds according to the invention are represented by the general formula:

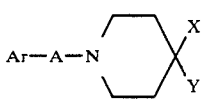
(I)

in which:
Ar represents a group

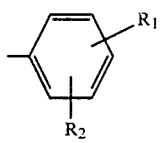

in which:
$R_1$ represents a hydrogen atom, a halogen atom, a trifluoromethyl group, a lower alkyl group (1 to 4 carbon atoms), a lower alkoxy group (1 to 4 carbon atoms), a nitro group, a cyano group or a hydroxyl group, and
$R_2$ represents H or a halogen atom, or alternatively
Ar represents a naphthyl group optionally substituted by a halogen atom;
A represents one of the following nitrogen-containing heterocyclic nuclei:

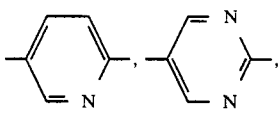

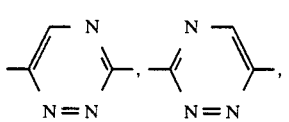

and
finally, X and Y, taken separately, denote a hydrogen atom in one case and a group $OR_3$ in the other, $R_3$ representing:
hydrogen,
a group

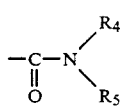

in which $R_4$ denotes hydrogen or a lower alkyl group (1 to 4 carbons) and $R_5$ denotes a lower alkyl group (1 to 4 carbons), or alternatively $R_4$ and $R_5$, together with the nitrogen atom to which they are bonded, denote the 4-hydroxypiperidino group, or a group —$COR_5$, in which $R_5$ is as above, or alternatively X and Y, taken together, form an oxo group (=O).

More precisely, the compounds according to the invention correspond to one of the following 4 formulae:

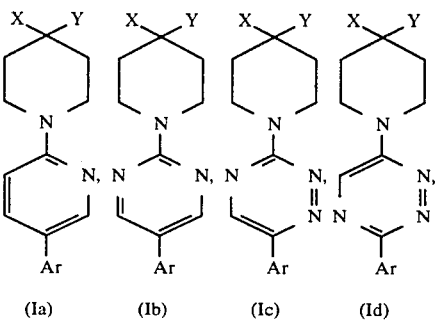

(Ia)   (Ib)   (Ic)   (Id)

in which the meanings of Ar, X and Y are as defined above.

The compounds are capable of giving addition salts with mineral or organic acids. These salts form an integral part of the invention.

In general, the compounds (I) are prepared from the corresponding halogenated derivative (most commonly the chlorinated derivative), with which an excess of the amine:

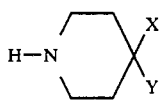

is reacted in a solvent such as an alkanol (ethanol, propanol, butanol or the like), with heating to a temperature of between 75° and 120° C.

If X and Y together represent an oxo group, this oxo group is preferably blocked in the form of an acetal before the amine is reacted with the halogenated derivative, if good results are to be obtained. After the amine has been condensed as indicated above, the oxo group is freed by treatment in an acid medium.

If X=H and Y represents a group:

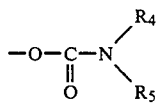

the compounds (I) can be obtained from the corresponding compounds in which X=H and Y=OH.

In a first stage, the corresponding activated ester is prepared by reaction with a chloroformate, such as phenyl chloroformate, by a known process:

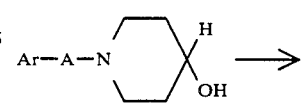

-continued

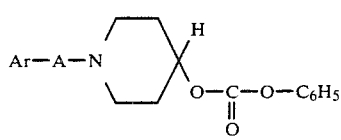

This activated ester is heated with the amine

in solution in an inert solvent, to give the compound (I) in which X=H and

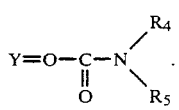

The compounds in which X is H and Y is a group O—CO—$R_5$ can be prepared by acylation of the corresponding compounds in which X=H and Y=OH, by a known process.

Finally, if the group Ar represents a hydroxyphenyl, the compounds (I) can be prepared by demethylation of the corresponding compounds (I) in which Ar represents a methoxyphenyl group.

The halogenated derivatives used to prepare the compounds according to the invention are known or can be prepared by known processes.

PYRIDINE DERIVATIVES

The chlorinated derivatives can be prepared as indicated in European Pat. No. 17438 according to the following reaction scheme:

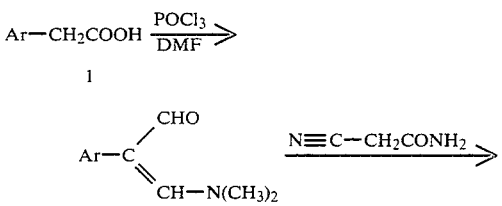

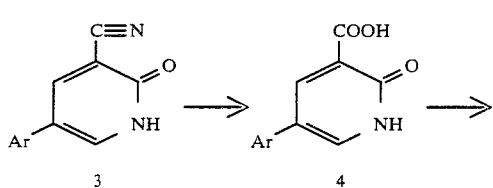

Treatment of an arylacetic acid 1 with phosphorus oxychloride and dimethylformamide gives the prop-2-enal derivative 2, which, when condensed with cyanoacetamide, gives the cyclic compound 3. By hydrolysis of the nitrile, this gives 4, which is decarboxylated to 5.

Finally, reaction with phosphorus oxychloride gives the expected halogenated derivative 6.

PYRIMIDINE DERIVATIVES

According to U.S. Pat. No. 4 209 621, the chlorinated pyrimidine derivatives can be prepared according to the following reaction scheme:

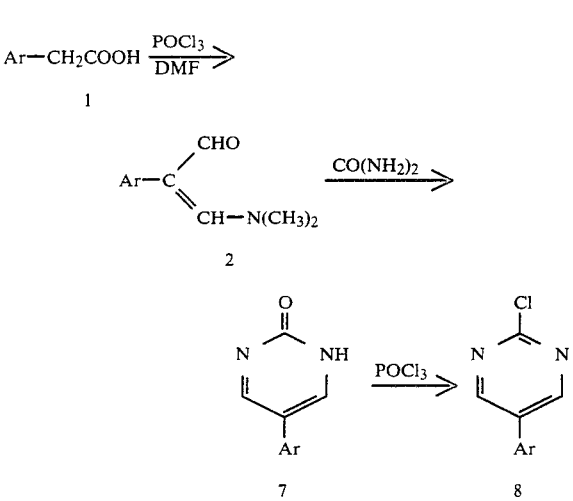

The first step, as indicated previously, gives the prop-2-enal 2. By reaction with urea, this gives the pyrimidinone 7, which, when treated with $POCl_3$, gives the desired chlorinated derivative.

1,2,4-TRIAZINE DERIVATIVES (a) Derivatives chlorinated in the 3-position

According to the method described in Journal of Heterocyclic Chemistry 16, 1392–1407 (1979), these compounds can be obtained according to the reaction scheme:

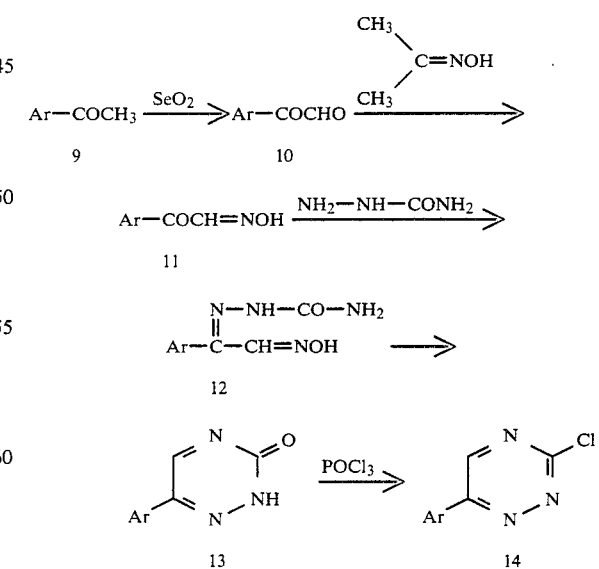

Oxidation of an acetophenone 9 with selenium dioxide gives the phenylglyoxal 10, which gives the corresponding oxime 11 using an oxime exchange method.

This oxime is converted to the semicarbazone 12, which is cyclized to 13 by heating in a dilute acid medium.

Reaction with phosphorus oxychloride gives the chlorinated derivative 14.

(b) Derivatives chlorinated in the 6-position

These derivatives can be obtained by following the technique described in the European Patent Application published under the number 80296.

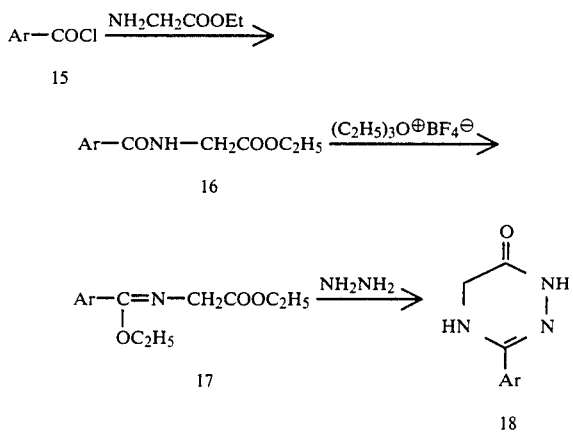

Reaction of ethyl glycinate hydrochloride with the acid chloride 15 gives the hippuric acid derivative 16. When treated with triethyloxonium fluoroborate, this gives 17, which is cyclized with hydrazine to give the tetrahydro-1,2,4-triazin-6-one 18.

Reaction of this compound with bromine in acetic acid gives the corresponding dihydro derivative, and reaction with phosphorus oxychloride then gives the chlorinated derivative:

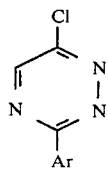

19

The examples which follow illustrate the invention without restricting its scope.

EXAMPLE 1

5-(2-Chlorophenyl)-2-(4-hydroxypiperidino)-pyridine acid maleate (SR 42482 A)

(a) 2-(2-Chlorophenyl)-3-dimethylaminoprop-2-enal 73 g of dimethylformamide are cooled to −50° C. 92 g of phosphorus oxychloride are added dropwise, followed by 34.2 g of 2-chlorophenylacetic acid, and the reaction mixture is stirred at room temperature for 30 minutes. It is then heated at 70°-80° C. for 5 hours 30 minutes. The reaction mixture is rendered alkaline with potassium carbonate, 200 ml of toluene are added and the mixture is heated in a water bath for 1 hour.

The organic phase is decanted, washed with water, decanted, dried over sodium sulfate and filtered and the filtrate is concentrated in vacuo. The residue is recrystallized from a mixture of isopropyl ether/methylene chloride.

Weight: 5.4 g; melting point: 86°-88° C.

(b) 5-(2-Chlorophenyl)-1,2-dihydro-2-oxopyridine-3-carbonitrile 3.3 g of sodium are dissolved in 150 ml of methanol. 6.1 g of cyanoacetamide are added to the solution, followed by 5.4 g of the product obtained above, and the reaction mixture is heated under reflux for 16 hours.

An insoluble material is filtered off, 10 ml of acetic acid and 500 ml of water are added to the mother liquor and the precipitate is filtered off and recrystallized from absolute ethanol.

Weight: 3.2 g; melting point: 254°-256° C.

(c) 5-(2-Chlorophenyl)-1,2-dihydro-2-oxopyridine-3-carboxylic acid 12.2 g of the product obtained above are heated under reflux in a mixture of 100 ml of hydrochloric acid and 100 ml of acetic acid for 16 hours.

The reaction mixture is cooled and the precipitate is filtered off, rinsed with water and dried in vacuo.

Weight: 12.4 g; melting point: above 260° C.

(d) 5-(2-Chlorophenyl)-1,2-dihydro-2-oxopyridine 12.4 g of the product obtained above, in 80 ml of quinoline, and 1.2 g of reduced copper are heated under reflux for 4 hours, with stirring.

The reaction mixture is poured into 1.5 liters of a 20% solution of hydrochloric acid and the precipitate is filtered off, rinsed with water, dried in vacuo and chromatographed on silica gel; eluent: ethyl acetate and then ethyl acetate/methanol 90/10.

The first 3 fractions are discarded as impurities and the next fraction is concentrated in vacuo.

Weight: 4.3 g; melting point: 156°-158° C.

(e) 2-Chloro-5-(2-chlorophenyl)pyridine 4.3 g of the product obtained above are heated under reflux in 100 ml of phosphorus oxychloride, in the presence of 0.5 ml of dimethylformamide, for 4 days.

The excess phosphorus oxychloride is concentrated in vacuo, the residue is taken up in a solution of sodium carbonate, the mixture is extracted with methylene chloride, the extract is decanted, dried over sodium sulfate and filtered and the filtrate is concentrated in vacuo.

The residue is chromatographed on silica gel; eluent: ethyl acetate. The first fraction is concentrated in vacuo.

Weight: 3 g; melting point: 100°-102° C.

(f) SR 42482 A 3 g of the product obtained above and 3.9 g of 4-hydroxypiperidine are heated under reflux in 100 ml of butanol for 48 hours.

The butanol is concentrated in vacuo, the residue is taken up in water, the mixture is extracted with ethyl acetate, the organic phase is decanted, dried over sodium sulfate and filtered and the filtrate is concentrated in vacuo. The residue is chromatographed on silica gel; eluent: ethyl acetate.

The first three fractions are discarded as impurities and the next fraction is concentrated in vacuo. The residue is taken up in 100 ml of ethyl acetate, 0.6 g of maleic acid is added, the mixture is heated to the boil and filtered and the maleate is left to crystallize.

Weight: 1.6 g; melting point: 140°-142° C.

EXAMPLE 2

5-(2,4-Dichlorophenyl)-2-(4-hydroxypiperidino)pyridine (SR 42903)

The following are obtained successively using the procedure of Example 1 but replacing the 2-chlorophenylacetic acid with an equivalent quantity of 2,4-dichlorophenylacetic acid:

2-(2,4-dichlorophenyl)-3-dimethylaminoprop-2enal; melting point: 112°–114° C. (ethyl acetate).

5-(2,4-dichlorophenyl)-1,2-dihydro-2-oxopyridine-3-carbonitrile; melting point: >260° C. (ethanol).

5-(2,4-dichlorophenyl)-1,2-dihydro-2-oxopyridine-3-carboxylic acid; melting point >260° C.

5-(2,4-dichlorophenyl)-1,2-dihydro-2-oxopyridine; melting point: 170°–172° C. (chromatographed).

2-chloro-5-(2,4-dichlorophenyl)pyridine; melting point: 150° C.

SR 42903 isolated in the form of the base; melting point: 132°–134° C. (isopropyl ether).

EXAMPLE 3

5-(2-Chlorophenyl)-2-(4-oxopiperidino)pyridine acid maleate (SR 42696 A)

(a)

5-(2-Chlorophenyl)-2-(1,4-dioxo-8-azaspiro[4,5]-decyl-8)pyridine 5 g of 2-chloro-5-(2-chlorophenyl)pyridine (Example 1e) and 9.58 g of 1,4-dioxa-8-azaspiro[4,5]-decane are heated under reflux in 100 ml of butanol for 6 days.

The butanol is concentrated in vacuo, the residue is taken up in water to which hydrochloric acid has been added, the mixture is washed with ether, the aqueous phase is rendered alkaline with a solution of sodium carbonate, the mixture is extracted with ethyl acetate, the organic phase is decanted, dried over sodium sulfate and filtered and the filtrate is concentrated in vacuo.

Weight: 3.1 g (brown oil).

(b) SR 42696 A 3.1 g of the product obtained above are heated under reflux in a solution of 60 ml of water and 40 ml of formic acid for 3 hours.

The reaction mixture is poured into an iced solution of sodium hydroxide, the resulting mixture is extracted with methylene chloride, the extract is decanted, dried over sodium sulfate and filtered and the filtrate is concentrated in vacuo.

The residue is chromatographed on silica gel; eluent: chloroform/methanol 95/5.

The first fraction is discarded, the second fraction is then concentrated in vacuo and the maleate is recrystallized from ethyl acetate.

Weight: 1.3 g; melting point: 146°–148° C.

EXAMPLE 4

5-(2-Chlorophenyl)-2-(4-hydroxypiperidino)pyrimidine (SR 42505)

(a) 5-(2-Chlorophenyl)-1,2-dihydro-2-oxopyrimidine 10 g of 2-(2-chlorophenyl)-3-dimethylaminoprop-2-enal (Example 1a) and 6 g of urea are heated under reflux in 40 ml of ethanol, in the presence of 10 ml of hydrochloric acid, for 4 hours.

The ethanol is concentrated in vacuo, the residue is taken up in water, the mixture is rendered alkaline with sodium hydroxide and the precipitate is filtered off and rinsed with ethanol and then with ether.

Weight: 11 g; melting point: above 260° C.

(b) 2-Chloro-5-(2-chlorophenyl)pyrimidine 11 g of the product obtained above are heated under reflux in 100 ml of phosphorus oxychloride for 2 hours.

The excess phosphorus oxychloride is concentrated in vacuo, the residue is taken up in water to which sodium carbonate has been added, the mixture is extracted with ethyl acetate, the extract is decanted, dried over sodium sulfate and filtered and the filtrate is concentrated.

Weight: 3.2 g; melting point: 152°–154° C.

(c) SR 42505

3.2 g of the product obtained above and 4.3 g of 4-hydroxypiperidine are heated under reflux in 100 ml of ethanol for 3 hours.

The ethanol is concentrated in vacuo, the residue is taken up in water to which sodium carbonate has been added, the mixture is extracted with ethyl acetate, the extract is decanted, dried over sodium sulfate and filtered and the filtrate is concentrated in vacuo.

The residue is chromatographed on silica gel; eluent: ethyl acetate. The first fraction is discarded as an impurity and the next fraction is concentrated in vacuo. The residue is recrystallized from isopropyl ether/methylene chloride.

Weight: 3.2 g; melting point: 122° C.

EXAMPLES 5 TO 9

The following compounds (respectively) likewise obtained successively using the procedure of Example 4 but varying the starting arylacetic acid:

$a_5$ 5-(2,4-dichlorophenyl)-1,2-dihydro-2-oxopyrimidine; melting point >260° C.

$a_6$ 5-(4-chlorophenyl)-1,2-dihydro-2-oxopyrimidine; melting point: about 140° C.

$a_7$ 5-(3-chlorophenyl)-1,2-dihydro-2-oxopyrimidine; melting point: 250°–252° C. (decomposition).

$a_8$ 5-(4-methoxyphenyl)-1,2-dihydro-2-oxopyrimidine; melting point: 258°–260° C.

$a_9$ 5-(naphthyl-1)-1,2-dihydro-2-oxopyrimidine; melting point: 260° C.

then during the course of the reaction the following compounds (respectively) are obtained:

$b_5$ 2-chloro-5-(2,4-dichlorophenyl)pyrimidine; melting point: 176°–178° C.

$b_6$ 2-chloro-5-(4-chlorophenyl)pyrimidine.

$b_7$ 2-chloro-5-(3-chlorophenyl)pyrimidine; melting point: 124°–126° C. (chromatography).

$b_8$ 2-chloro-5-(4-methoxyphenyl)pyrimidine; melting point: 132°–134° C.

$b_9$ 2-chloro-5-(naphthyl-1)pyrimidine chromatographed on silica (eluent: methylene chloride).

and finally as end products the following compounds (respectively) are obtained:

$c_5$ 5-(2,4-dichlorophenyl)-2-(4-hydroxypiperidino)-pyrimidine (SR 42824); melting point: 122°–124° C. (isopropyl ether).

$c_6$ 5-(4-chlorophenyl)-2-(4-hydroxypiperidino)pyrimidine (SR 42921); melting point: 168°–170° C. (ethyl acetate).

$c_7$ 5-(3-chlorophenyl)-2-(4-hydroxypiperidino)pyrimidine (SR 42922); melting point: 160°–162° C. (ethyl acetate).

c₈ 5-(4-methoxyphenyl)-2-(4-hydroxypiperidino)pyrimidine (SR 43159); melting point: 158°–160° C. (ethanol).

c₉ 5-(naphthyl-1)-2-(4-hydroxypiperidino)pyrimidine (SR 43139); melting point: 130°–132° C. (isopropyl ether).

EXAMPLE 10

2-(4-Acetoxypiperidino)-5-(2,4-dichlorophenyl)pyrimidine (SR 43651)

6 g of 2-(4-hydroxypiperidino)-5-(2,4-dichlorophenyl)pyrimidine (Example 5) and 60 ml of acetic anhydride are heated under reflux for 4 hours.

The mixture is evaporated to dryness in vacuo and the residue is taken up in a 10% aqueous solution of sodium carbonate. The mixture is extracted with methylene chloride and the solution is dried over sodium sulfate and concentrated to dryness in vacuo. The residue is chromatographed on silica gel. Elution with methylene chloride gives the expected product.

After recrystallization from isopropyl ether, melting point: 100°–102° C.; weight: 1.1 g.

EXAMPLE 11

2-(4-Methylcarbamoyloxypiperidino)-5-(2-chlorophenyl)pyrimidine (SR 43543)

(a) 2-(4-Phenoxycarbonyloxypiperidino)-5-(2-chlorophenyl)pyrimidine 11.4 ml of phenyl chloroformate are added slowly to a solution of 12.7 g of 5-(2-chlorophenyl)-2-(4-hydroxypiperidino)pyrimidine (Example 4) in 50 ml of pyridine, cooled to 5° C. After the addition has ended, the mixture is heated at 60° C. for 3 hours.

The pyridine is evaporated off in vacuo. The residue is taken up in dilute sodium hydroxide solution and the mixture is extracted with methylene chloride. The solution is dried over sodium sulfate and the solvent is then evaporated off in vacuo.

The residue is chromatographed on a column of silica gel. Elution with ethyl acetate gives the expected product, which is crystallized from ethyl acetate; melting point: 114°–116° C.; weight: 11.5 g.

(b) SR 43543

A mixture of 4.1 g of the product obtained above and 3 ml of a 40% aqueous solution of methylamine in 80 ml of acetone is heated under reflux for 18 hours. The acetone is evaporated off in vacuo and the residue is taken up in a dilute aqueous solution of hydrochloric acid. The mixture is extracted with ethyl acetate and the aqueous phase is separated off and rendered alkaline with aqueous ammonia. The mixture is extracted with ethyl acetate and the solution is dried over sodium sulfate. The solvent is evaporated off in vacuo and the residue is crystallized from pentane. Recrystallization from ether gives 1.1 g of the expected product; melting point: 104°–106° C.

EXAMPLES 12 AND 13

The following are obtained using the procedure of Example 11 (b), starting from the activated ester prepared under (a) but varying the amine:

2-(4-dimethylcarbamoyloxypiperidino)-5-(2-chlorophenyl)pyrimidine (SR 43537).

Melting point: 86°–88° C. (isopropyl ether).

2-[4-(4-hydroxypiperidinocarbonyloxy)piperidino]-5-(2-chlorophenyl)pyrimidine (SR 43516).

Melting point: 124°–126° C. (ethyl acetate).

EXAMPLE 14

2-(4-Dimethylcarbamoyloxypiperidino)-5-(2,4-dichlorophenyl)pyrimidine (SR 43539)

(a) 2-(4-Phenoxycarbonyloxypiperidino)-5-(2,4-dichlorophenyl)pyrimidine

Prepared according to Example 11 (a) starting from the hydroxylated compound of Example 5.

Melting point: 168°–170° C. (ethyl acetate).

(b) SR 43539

Prepared as in Example 11 (b) starting from the compound prepared above and dimethylamine.

Melting point: 122°–124° C. (hexane).

EXAMPLE 15

6-(2-Chlorophenyl)-3-(4-hydroxypiperidino)-1,2,4-triazine (SR 42524)

7.4 g of 3-chloro-6-(2-chlorophenyl)-1,2,4-triazine, prepared according to J. Het. Chem. 16, 1402 (1979), and 9 g of 4-hydroxypiperidine are heated under reflux in 150 ml of ethanol for 3 hours.

The ethanol is concentrated in vacuo, the residue is taken up in water, the mixture is rendered alkaline with a 10% solution of sodium carbonate and extracted with ethyl acetate, the organic phase is decanted, dried over sodium sulfate and filtered and the filtrate is concentrated in vacuo.

The residue is recrystallized from ethyl acetate.

Weight: 5.4 g; melting point: 162°–164° C.

EXAMPLE 16

6-(2,4-Dichlorophenyl)-3-(4-hydroxypiperidino)-1,2,4-triazine (SR 42825)

(a) (2,4-Dichlorophenyl)glyoxaldoxime 36.4 g of selenium oxide are dissolved in 245 ml of dioxane in the presence of 7.3 ml of water. 60.4 g of 2,4-dichloroacetophenone are added and the reaction mixture is heated under reflux for 18 hours, with stirring. The solution is filtered, 100 ml of water are added and the pH is adjusted to 4–5 with a 5% solution of sodium hydroxide.

24.6 g of acetoxime are then added and the reaction mixture is stirred at room temperature for 8 days.

The mixture is filtered a second time, the dioxane is concentrated in vacuo, the residue is taken up in water, the mixture is extracted with ether, the extract is decanted, dried over sodium sulfate and filtered and the filtrate is concentrated in vacuo.

Weight: 62.2 g of a yellow oil.

(b) (2,4-Dichlorophenyl)glyoxaldoxime semicarbazone 62 g of the product obtained above, 31.8 g of semicarbazide hydrochloride and 38.9 g of sodium acetate trihydrate are heated at 50° C. in 350 ml of 50% ethanol for 2 and a half hours, with stirring.

The reaction mixture is cooled and the precipitate is filtered off.

Weight: 75 g.

(c) 6-(2,4-Dichlorophenyl)-2,3-dihydro-3-oxo-1,2,4-triazine 75 g of the product obtained above are heated under reflux in 2 liters of 5% hydrochloric acid for 1 hour.

The precipitate is filtered off and heated under reflux in 350 ml of acetic acid for 18 hours. The acetic acid is concentrated in vacuo, the residue is taken up in water and the precipitate is filtered off, taken up in ethanol, filtered off and dried in vacuo.

Weight: 36 g; melting point: about 160° C.

(d) 3-Chloro-6-(2,4-dichlorophenyl)-1,2,4-triazine 18 g of the product obtained above are heated under reflux in 180 ml of phosphorus oxychloride, in the presence of 2 ml of dimethylformamide, for 3 and a half hours.

The excess phosphorus oxychloride is concentrated in vacuo, the residue is taken up in water, the mixture is extracted with ethyl acetate, the extract is decanted, dried over sodium sulfate and filtered and the filtrate is concentrated in vacuo.

Weight: 15.7 g.

(e) SR 42825

7.8 g of the product obtained above and 9.1 g of 4-hydroxypiperidine are heated under reflux in 150 ml of absolute ethanol for 6 hours.

The ethanol is concentrated in vacuo, the residue is taken up in water, the mixture is rendered alkaline with a solution of sodium carbonate and extracted with ethyl acetate, the extract is decanted, dried over sodium sulfate and filtered and the filtrate is concentrated in vacuo.

The residue is chromatographed on silica gel; eluent: ethyl acetate. The first fractions are discarded as impurities and the next fraction is concentrated in vacuo. The residue is recrystallized from ethyl acetate.

Weight: 1.4 g; melting point: 128°-130° C.

EXAMPLE 17

6-(2-Chlorophenyl)-3-(4-oxopiperidino)-1,2,4-triazine (SR 42642)

1.5 g of 3-chloro-6-(2-chlorophenyl)-1,2,4-triazine, 3.05 g of piperidin-4-one monohydrate hydrochloride and 3.1 g of sodium carbonate are heated under reflux in 100 ml of ethanol for 4 hours.

The ethanol is concentrated in vacuo, the residue is taken up in water, the mixture is extracted with ethyl acetate, the extract is decanted, dried over sodium sulfate and filtered and the filtrate is concentrated in vacuo. The residue is chromatographed on silica gel; eluent: ethyl acetate.

The first fraction is concentrated in vacuo. The residue is recrystallized from isopropyl ether/methylene chloride.

Weight: 0.9 g; melting point: 170°-172° C.

EXAMPLE 18

6-(2,4-Dichlorophenyl)-3-(4-oxopiperidino)-1,2,4-triazine (SR 42826)

The procedure of Example 17 is followed starting from the chlorinated derivative obtained in Example 16 (d). The expected product is isolated in the same manner.

Melting point: 120°-122° C. (isopropyl ether/methylene chloride).

EXAMPLE 19

3-(4-Chlorophenyl)-6-(4-hydroxypiperidino)-1,2,4-triazine (SR 42833)

(a) Ethyl N-(4-chlorobenzoyl)aminoacetate 30 g of 4-chlorobenzoyl chloride and 50.2 g of ethyl glycinate hydrochloride are heated under reflux in 150 ml of benzene for 8 hours, with stirring.

The reaction mixture is poured into a dilute solution of sodium carbonate and extracted with ethyl acetate, the organic phase is decanted, dried over sodium sulfate and filtered and the filtrate is concentrated in vacuo. The residue is taken up in isopropyl ether and the precipitate is filtered off.

Weight: 60.5 g; melting point: 118° C.

(b) Ethyl N-(ethoxycarbonylmethyl)-4-chlorobenzimidate 44 g of the product obtained above and 50.7 g of triethyloxonium tetrafluoroborate are dissolved in 250 ml of methylene chloride and the solution is stirred at room temperature for 6 days. A solution of 37.6 g of potassium carbonate in 70 ml of water is added dropwise, with stirring, the mixture is diluted with 200 ml of methylene chloride, the organic phase is decanted, dried over sodium sulfate and filtered and the filtrate is concentrated in vacuo.

The residue is taken up in petroleum ether, an insoluble material is filtered off and the mother liquor is concentrated in vacuo.

Weight: 35.4 g of a yellow oil.

(c) 3-(4-Chlorophenyl)-1,4,5,6-tetrahydro-6-oxo-1,2,4-triazine 35.4 g of the product obtained above and 12.75 ml of hydrazine hydrate are heated under reflux in 300 ml of absolute ethanol for 2 hours.

The reaction mixture is left to cool and the precipitate is filtered off and recrystallized from methanol.

Weight: 14.4 g; melting point: above 260° C.

(d) 3-(4-Chlorophenyl)-1,6-dihydro-6-oxo-1,2,4-triazine 3 g of the product obtained above are suspended in 30 ml of acetic acid and the suspension is heated to 40° C., with stirring. A solution of 0.8 ml of bromine in 10 ml of acetic acid is added dropwise at this temperature and the reaction mixture is then heated under reflux for half an hour.

The acetic acid is concentrated in vacuo, the residue is taken up in water, the mixture is extracted with ethyl acetate, the extract is washed with a dilute solution of hydrochloric acid, decanted, dried over sodium sulfate and filtered and the filtrate is concentrated in vacuo.

Weight: 1.5 g.

(e) 6-Chloro-3-(4-chlorophenyl)-1,2,4-triazine 1.5 g of the product obtained above are heated under reflux in 30 ml of phosphorus oxychloride for 4 hours. The excess phosphorus oxychloride is concentrated in vacuo, the residue is taken up in iced water, the mixture is extracted with methylene chloride, the extract is decanted, dried over sodium sulfate and filtered and the filtrate is concentrated in vacuo.

Weight: 1.2 g.

(f) SR 42833

1.2 g of the product obtained above are heated under reflux in 30 ml of absolute ethanol, in the presence of 1.6 g of 4-hydroxypiperidine, for 5 hours.

The ethanol is concentrated in vacuo, the residue is taken up in water, the mixture is rendered alkaline with a solution of sodium carbonate and extracted with methylene chloride, the organic phase is decanted, dried over sodium sulfate and filtered and the filtrate is concentrated in vacuo. The residue is recrystallized from absolute ethanol.

Weight: 0.75 g; melting point: 188°–190° C.

EXAMPLE 20

3-(3-Chlorophenyl)-6-(4-hydroxypiperidino)-1,2,4-triazine (SR 42904)

The procedure of Example 19 is followed replacing the 4-chlorobenzoyl chloride with 3-chlorobenzoyl chloride in the first step.

The following are thus isolated in succession:
ethyl N-(3-chlorobenzoyl)aminoacetate; melting point: 70°–72° C. (isopropyl ether).
3-(3-chlorophenyl)-1,4,5,6-tetrahydro-6-oxo-1,2,4-triazine; melting point: 228°–230° C. (absolute ethanol).
SR 42904; melting point: 142°–144° C. (ethyl acetate).

The compounds according to the invention were studied for their pharmacological properties. In particular, they were subjected to the following tests:

1—EVALUATION OF THE ANTICONVULSANT ACTIVITY

The anticonvulsant effect of the products on mice was evaluated on a model involving convulsions caused by an electric shock and on a model involving convulsions induced by a chemical agent: bicuculline.

(a) Antagonism towards the convulsions induced by an electric shock

The test was a slightly modified version of that of SWINYARD et al. [Journal of Pharmacology and Experimental Therapeutics 106, 319–330 (1952)] and ASAMI et al. [Arzneimittel Forschung 24(10), 1563–1568 (1974)]. The equipment consisted of a Racia shock generator fitted with 2 ocular electrodes delivering a current at 12.5 volts for 0.3 second. The groups consisted of 10 CDI Charles River mice weighing between 20 and 24 g.

The products were administered orally 60 minutes before the electric shock. Those animals which did not show tonic extension of the rear limbs were considered to be protected from convulsive seizure.

| Products | Median effective dose (ED$_{50}$) (1) for antagonism towards electric shock (mg/kg, administered orally) |
|---|---|
| SR 42 903 | 28 (25–32) |
| SR 42 904 | 59 (42–82) |
| SR 42 524 | 24 (18–32) |
| SR 42 642 | 40 (33–49) |
| SR 42 825 | 16 (8–29) |
| SR 42 826 | 26 (19–35) |
| SR 42 505 | 42 (36–50) |
| SR 42 824 | 20 (16–26) |
| SR 43 139 | 43 (37–51) |
| SR 43 159 | 83 (63–108) |
| SR 43 516 | 91 (57–122) |
| SR 43 543 | 19 (12–43) |
| SR 43 537 | 2.5 (0.9–3.4) |

-continued

| Products | Median effective dose (ED$_{50}$) (1) for antagonism towards electric shock (mg/kg, administered orally) |
|---|---|
| SR 43 539 | 2.5 (1.8–3.6) |
| SR 43 651 | 43 (31–56) |

(1): The ED$_{50}$ was calculated by the probit method; the confidence limits in brackets were established for the probability level $p \leq 0.05$.

(b) Antagonism towards the convulsions and the mortality caused by bicuculline

The groups consisted of 10 CDI Charles River mice weighing between 20 and 22 g. The products were administered orally 60 minutes before the bicuculline (0.8 mg/kg, administered intravenously). The appearance of tonic convulsions, as well as mortality, were noted for 60 minutes following injection of the bicuculline.

| Products | Median effective dose (ED$_{50}$) (1) for antagonism towards bicuculline (mg/kg, administered orally) | |
|---|---|---|
| | Tonic convulsions | Mortality |
| SR 42 524 | 71 (58–87) | 72 (56–94) |
| SR 42 825 | 3.1 (2.3–3.7) | 3.3 (2.5–4.3) |
| SR 42 826 | 3.2 (2–5) | 3.4 (2.3–5) |
| SR 42 505 | 52 (38–72) | 54 (40–73) |
| SR 42 824 | 9.4 (7.8–11.5) | 8 (6.1–10.5) |
| SR 43 139 | 46 (35–59) | 44 (34–57) |
| SR 43 159 | 70 (48–101) | 60 (47–77) |
| SR 43 543 | 4.3 (3.1–5.8) | 3.9 (0.6–5.8) |
| SR 43 537 | 3.3 (2.4–5.2) | 3.0 (2.1–4.5) |
| SR 43 539 | 1.1 (0.5–2.8) | 0.7 (0.3–1.4) |
| SR 43 651 | 17.2 (11–32) | 15.5 (10–27) |

(1): The ED$_{50}$ was calculated by the probit method; the confidence limits in brackets were established for the probability level $p \leq 0.05$.

After oral administration to mice, the products according to the invention exhibit anticonvulsant properties towards both electric shock and bicuculline.

2—EVALUATION OF THE ANALGESIC ACTIVITY OF THE PRODUCTS

The analgesic activity of the products according to the invention was evaluated using the KOSTER test (Federation Proceeding 18, 41 (1959)).

The products were administered orally to mice 30 minutes before the intraperitoneal injection of 0.25 ml of 0.1N acetic acid dissolved in 10% gum arabic. The contortions between the fifth and tenth minute and between the fifteenth and twentieth minute after administration of the acid were counted for the control animals and the treated animals.

| Products | Dose mg/kg, administered orally | Antagonism towards the contortional movements (percent/control animals) |
|---|---|---|
| SR 42 482 | 25 | −50% |
| SR 42 833 | 25 | −31% |
| SR 42 825 | 25 | −57% |
| SR 42 826 | 25 | −42% |
| SR 42 505 | 25 | −36% |
| SR 42 824 | 25 | −80% |

The products according to the invention are capable of antagonizing the contortional movements caused by the administration of acetic acid to mice; this effect is predictive of an analgesic activity.

3—EVALUATION OF THE ANTITHROMBOTIC ACTIVITY

The products of the present invention exhibited an antithrombotic activity on animals. For example, SR 42524 (200 mg/kg, administered orally) protected mice from mortality following the injection of collagen.

4—DETERMINATION OF THE LETHAL DOSE IN MICE AFTER ACUTE ADMINISTRATION

The products were administered orally to groups of 5 female CDI Charles River mice weighing between 20 and 24 g. They were solubilized in 0.1N HCl. The toxicity was recorded for 72 hours following the administration of the products.

|  | Percent toxicity or $LD_{50}$ | | |
| --- | --- | --- | --- |
| Products | 250 mg/kg, administered orally | 500 mg/kg, administered orally | 1000 mg/kg, administered orally |
| SR 42 482 | 0 | 0 | 0 |
| SR 42 696 | 0 | 0 | — |
| SR 42 904 | 0 | 0 | |
| SR 42 833 | 0 | 0 | — |
| SR 42 524 | 0 | 0 | 0 |
| SR 42 642 | 0 | 0 | — |
| SR 42 825 | 20 | 20 | 80 |
| SR 42 826 | 0 | 20 | — |
| SR 42 505 | 0 | 0 | 80 |
| SR 42 824 | 0 | 0 | — |
| SR 42 921 | 0 | 0 | — |
| SR 42 922 | 0 | 0 | 0 |
| SR 43 139 | 0 | 0 | 0 |
| SR 43 159 | 0 | 0 | 0 |
| SR 43 516 | 0 | 0 | 0 |
| SR 43 543 | 0 | 0 | 20 |

The results, expressed as the percentage of animals which die within 72 hours following oral administration of the products, are given in the table above.

The lethal doses of these derivatives are therefore considerably higher than their active doses in the pharmacological tests described in the above paragraphs.

The tests performed in this way show that the products according to the invention have valuable pharmacological properties and a low toxicity. Consequently, they can be used in human therapy, especially for the treatment of psychic, neurological, neuromuscular, cardiovascular and inflammatory complaints.

In particular, the products according to the invention can be used for the treatment of pain, anxiety states, insomnia, epilepsy, blood clotting disorders and also inflammatory diseases.

These products can be administered orally or by injection. The pharmaceutical compositions can be solid or liquid and can be, for example, in the form of tablets, gelatin capsules, granules, suppositories or injectable preparations.

The dosage can vary within wide proportions, depending in particular on the type and severity of the complaint to be treated and on the method of administration. Most commonly, for oral administration to adults, the dosage is between 1 mg and 500 mg per day, optionally divided up into several individual doses.

What is claimed is:

1. A compound with a nitrogen-containing heterocyclic nucleus, of the formula:

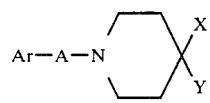

in which:

Ar represents a group

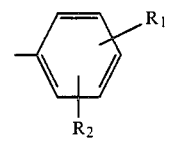

in which:

$R_1$ represents a hydrogen atom, a halogen atom, a trifluoromethyl group, a lower alkyl group (1 to 4 carbon atoms), a lower alkoxy group (1 to 4 carbon atoms), a nitro group, a cyano group or a hydroxyl group, and $R_2$ represents H or a halogen atom, or alternatively Ar represents a naphthyl group optionally substituted by a halogen atom;

A represents one of the following nitrogen-containing heterocyclic nuclei:

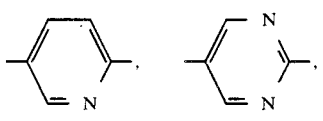

and

X and Y, taken separately, represent a hydrogen atom in one case and a group $-OR_3$ in the other, $R_3$ representing:

a hydrogen atom, a group

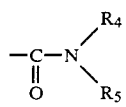

in which $R_4$ represents hydrogen or a lower alkyl group (1 to 4 carbons) and $R_5$ represents a lower alkyl group, or alternatively

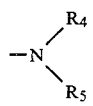

represents a 4-hydroxypiperidino group, or a group

in which R$_5$ is as defined above, or alternatively X and Y, taken together, form an oxo group (=O), and addition salts of the said compound with mineral or organic acids.

2. A pharmaceutical composition acting on the central nervous system, which contains at least one compound as claimed in claim 1, in combination with a pharmaceutically acceptable vehicle.

3. A pharmaceutical composition acting on the central nervous system, and which is in a form suitable for oral administration and which contains, per unit, from 1 to 500 mg of a compound as claimed in claim 1, in combination with a pharmaceutically acceptable vehicle.

4. A compound as claimed in claim 1, which is 5-(2,4-dichlorophenyl)-2- (4-hydroxypiperidino)-pyrimidine.

5. A compound as claimed in claim 1, which is 2-(4-acetoxypiperidino)-5-(2,4-dichlorophenyl)-pyrimidine.

6. A compound as claimed in claim 1, which is 2-(4-methylcarbamoyloxypiperidino)-5-(2-chlorophenyl)-pyrimidine.

7. A compound as claimed in claim 1, which is 2-(4-dimethylcarbamoyloxypiperidino)-5-(2-chlorophenyl)-pyrimidine.

8. A compound as claimed in claim 1, which is 2-(4-dimethylcarbamoyloxypiperidino)-5-(2,4-dichlorophenyl)pyrimidine.

9. A compound as claimed in claim 1, which is 6-(2-chlorophenyl)-3-(4-hydroxypiperidino)-1,2,4-triazine.

10. A compound as claimed in claim 1, which is 6-(2,4-dichlorophenyl)-3-(4-hydroxypiperidino)-1,2,4-triazine.

11. A compound as claimed in claim 1, which is 6-(2,4-dichlorophenyl)-3-(4-oxopiperidino)-1,2,4-triazine.

* * * * *